(12) United States Patent  
Schifman et al.

(10) Patent No.: US 8,412,375 B2
(45) Date of Patent: Apr. 2, 2013

(54) MEDICATION DISPENSING APPARATUS

(75) Inventors: Edward J. Schifman, Leawood, KS (US); Matthew J. Beck, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 456 days.

(21) Appl. No.: 12/036,876

(22) Filed: Feb. 25, 2008

(65) Prior Publication Data

US 2008/0264962 A1    Oct. 30, 2008

Related U.S. Application Data

(60) Provisional application No. 60/891,417, filed on Feb. 23, 2007.

(51) Int. Cl.
G07F 17/00 (2006.01)
B65D 83/04 (2006.01)

(52) U.S. Cl. ......... 700/237; 700/241; 700/242; 700/232

(58) Field of Classification Search ........... 700/231–244
See application file for complete search history.

(56) References Cited

U.S. PATENT DOCUMENTS

| | | | | |
|---|---|---|---|---|
| 3,719,272 A * | 3/1973 | Bodine et al. | ................ | 206/701 |
| 4,109,789 A * | 8/1978 | Fattori et al. | ................ | 206/404 |
| 4,433,882 A * | 2/1984 | Brown | ................ | 312/111 |
| 4,616,752 A * | 10/1986 | Ridgley | ................ | 206/533 |
| 5,137,340 A * | 8/1992 | Cugley et al. | ................ | 312/234.5 |
| 5,360,093 A * | 11/1994 | Baer | ................ | 194/206 |
| 5,466,058 A * | 11/1995 | Chan | ................ | 312/111 |
| 5,520,450 A * | 5/1996 | Colson et al. | ................ | 312/215 |
| 5,905,653 A * | 5/1999 | Higham et al. | ................ | 700/244 |
| 5,912,818 A * | 6/1999 | McGrady et al. | ................ | 700/232 |
| 6,109,774 A * | 8/2000 | Holmes et al. | ................ | 700/231 |
| 6,385,505 B1 * | 5/2002 | Lipps | ................ | 700/231 |
| 6,695,418 B2 * | 2/2004 | Skov et al. | ................ | 312/107 |
| 6,814,256 B2 * | 11/2004 | Clark | ................ | 221/79 |
| 6,840,378 B2 * | 1/2005 | Toguchi | ................ | 206/503 |
| 7,262,698 B1 * | 8/2007 | Frederick et al. | ................ | 340/545.6 |
| 7,318,630 B2 * | 1/2008 | Landsberger et al. | ................ | 312/111 |
| 7,463,947 B1 * | 12/2008 | Frederick et al. | ................ | 700/236 |
| 7,523,827 B2 * | 4/2009 | Dane et al. | ................ | 206/503 |
| 2002/0074905 A1 * | 6/2002 | Tiramani et al. | ................ | 312/108 |
| 2007/0069491 A1 * | 3/2007 | Ferraro et al. | ................ | 280/79.11 |
| 2008/0042534 A1 * | 2/2008 | Mallouk | ................ | 312/309 |
| 2009/0242582 A1 * | 10/2009 | Vlastakis et al. | ................ | 221/123 |

* cited by examiner

*Primary Examiner* — Michael K Collins
(74) *Attorney, Agent, or Firm* — Shook, Hardy & Bacon L.L.P.

(57) ABSTRACT

A medication dispenser provides automation to the steps of locating and acquiring medications or supplies to be administered to a patient. The medication dispenser includes one or more modules housing one or more compartmentalized drawers. Access to each drawer is controlled by a lockable door, and each the drawer may only be slid from the module housing the drawer in response to a signal. A series of lights direct the user to the appropriate drawer and the appropriate compartment of the relevant drawer to remove the appropriate medication or supply.

18 Claims, 4 Drawing Sheets

MEDICATION DISPENSING APPARATUS

CROSS-REFERENCE TO RELATED APPLICATIONS

This application claims the benefit of U.S. Provisional Application No. 60/891,417, filed Feb. 23, 2007, which is herein incorporated by reference in its entirety.

STATEMENT REGARDING FEDERALLY SPONSORED RESEARCH OR DEVELOPMENT

Not Applicable

BACKGROUND

As reported by the Institute of Medicine, an estimated 106,000 deaths occurred in 1994 due to adverse drug reactions (ADRs), and more than 2,000,000 hospitalized patients experienced serious, if not fatal, ADRs. Lazarou J. et al., *Incidence of adverse drug reactions in hospitalized patients: a meta-analysis of prospective studies*, J. Am. Med. Assn. 1998: 279: 1200-1205. Many of these errors are attributable to the systems and methods used to store and deliver medications to those clinicians providing care to patients. Various solutions have been proposed to address the issue of medication delivery errors. For instance, computerized systems ensure that the medication ordered or prescribed by the clinician is clinically appropriate. These systems may verify that the dosage is proper based on patient information such as weight and evidence based guidelines or protocols. Also, these systems may perform interaction checking against other medications. However, even if the clinician orders an acceptable medication and dosage amount for a specific patient, the actual drug and/or dosage administered to the patient may vary from what was requested. A pharmacist or other clinician may accidentally provide an improper drug or drug dosage if the order is not properly communicated and followed at each step in the clinical process. Errors may also occur during the steps of the medication administration process occurring between the pharmacy and the point of care. Existing systems and methods for physically transferring and storing and electronically tracking medications and supplied have been employed include automated dispensing machines (ADMs). To administer a medication to a patient, a nurse or other clinician retrieves the appropriate medication from one of a number of ADMs located throughout the healthcare facility. In addition to failing to prevent medication errors, existing systems and methods employing ADMs are wasteful and oftentimes difficult to use. The same issues apply when dispensing supplies.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention are directed to an automated medication dispenser. A medication dispenser provides automation to the steps of locating and acquiring medications or supplies to be administered to a patient or used during patient care. The medication dispenser includes one or more modules housing one or more compartmentalized drawers. Access to each drawer is controlled by a lockable door, and each drawer may only be slid from the module housing the drawer in response to a signal. A series of lights direct the user to the appropriate drawer and the appropriate compartment of the relevant drawer to remove the appropriate medication or supply.

BRIEF DESCRIPTION OF THE SEVERAL VIEWS OF THE DRAWINGS

In the accompanying drawings, which form a part of the specification and are to be read in conjunction therewith and in which like reference numerals are employed to indicate like parts in the various views.

DETAILED DESCRIPTION

Figure 1:
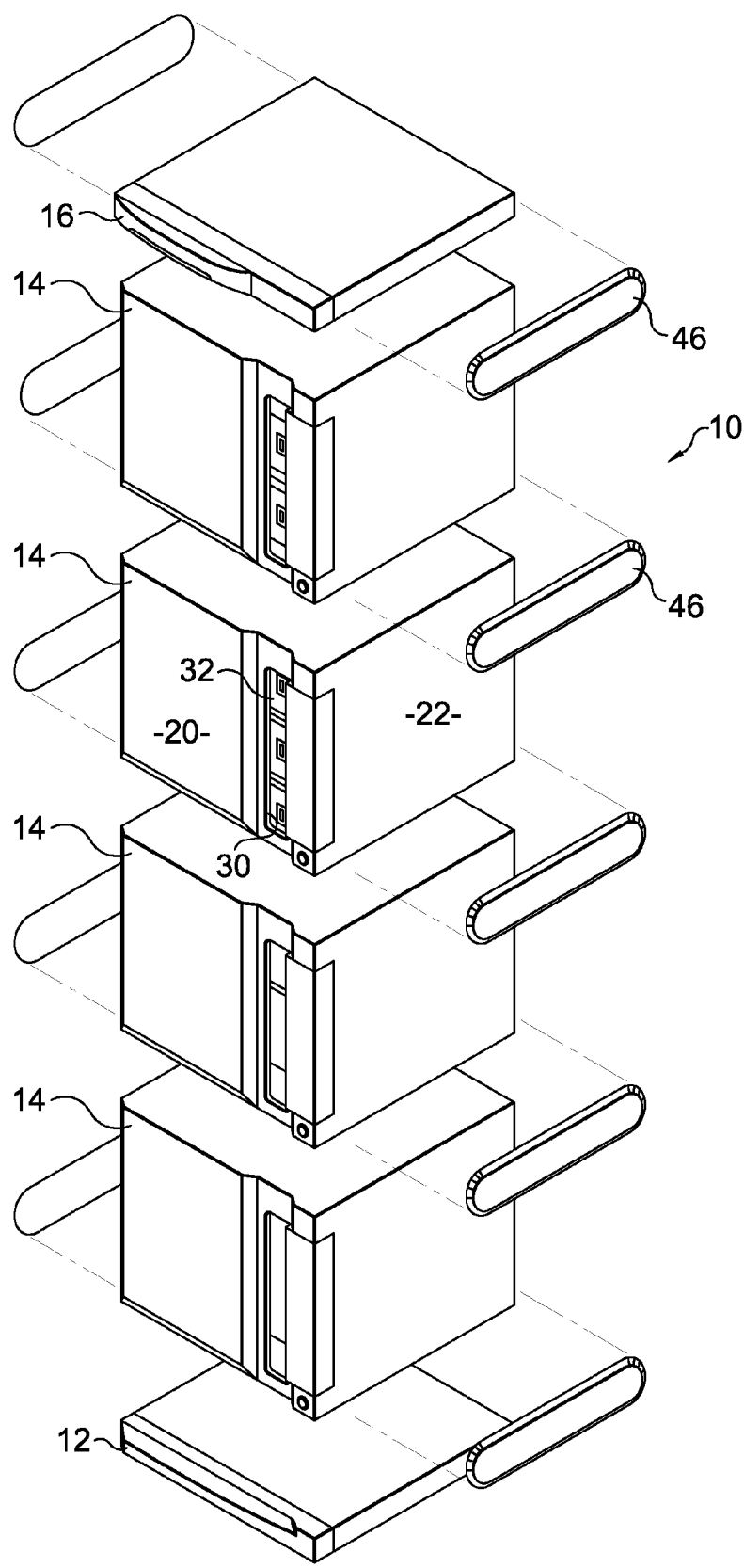
FIG. 1 is a front perspective view of a medication dispenser in accordance with an embodiment of the present invention.

With reference to the drawings, wherein like reference characters designate like parts throughout the different views, a medication and supply dispenser according to an embodiment of the present invention is designated generally with the reference numeral 10. The medication dispenser 10 generally includes a footer plate 12, a number of modules 14 and a header plate 16, as depicted in FIGS. 1-5. The modules 14 are disposed in a vertical stack, and each module contains a number of compartmentalized drawers 18 for storing and dispensing medical items which may include, for instance, medications in syringes, ampules, vials, oral suspensions, tubes, jars, oral solids and other packaging options, as well as a variety of medical supplies and other materials used in the provision of healthcare.

Each module 14 provides a controlled environment in which medications are stored. Each module 14 includes a front door 20 (that may be locked to regulate access to the drawers 18), side walls 22, a rear wall 24, a top 26, and a bottom 28. In some embodiments, a refrigeration unit (not shown) may be coupled with one or more of the modules 14, which may be desirable to avoid spoilage of certain types of medication.

Each front door 20 is lockable to limit access to only authorized clinicians. The door is hinged to one of the sidewalls 22 to rotate between a closed position as shown in FIG. 1 and an open position in FIG. 2. As shown in FIG. 1, each front door includes an opening 30 within which a window 32 is fixed. The window is transparent and allows a user to view a portion of each drawer as set forth in detail below.

Figure 4:
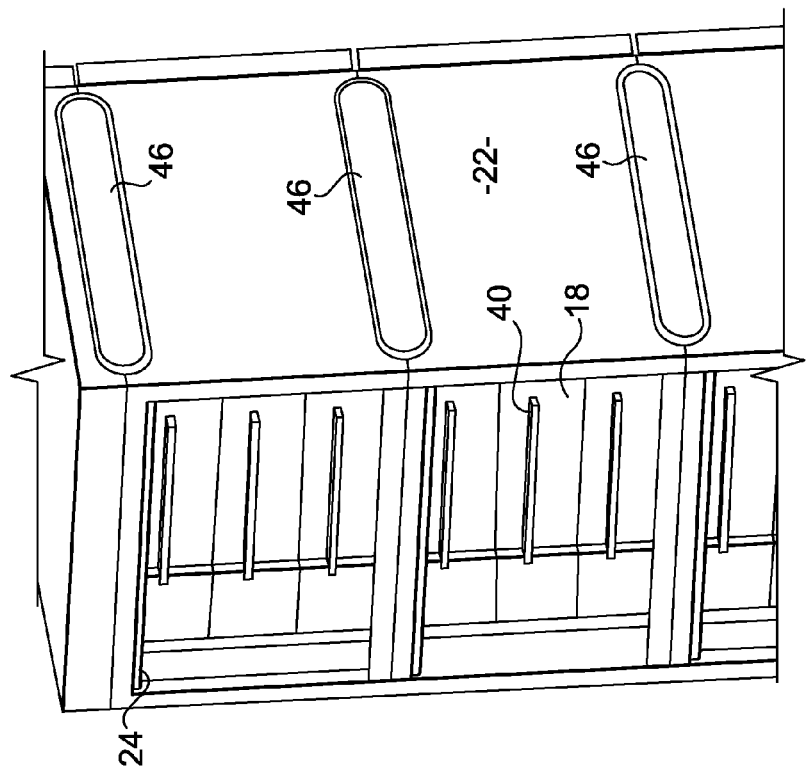
FIG. 4 is a rear perspective view of a medication dispenser in accordance with an embodiment of the present invention with sections removed to demonstrate the construction and assembly of the modules of the medication dispenser.

When the front door is open, access is provided to the drawers 18. Each drawer 18 may be slid from the module associated with the drawer when the front door 20 is open and the lock (not shown) for the particular drawer is unlocked. Specifically, when unlocked, a handle 33 of the drawer 18 may be grasped by the user to slide the drawer to an open position to allow access to a number of compartments 34 defined with the drawer 18. The medications, supplies and other materials are stored within the compartments. Also, as described in operation below, each drawer includes a signal light 36, and a number of selection lights 38 associated with each compartment 34. In embodiments, the signal lights 36 and selection lights 38 are electronically coupled with a master circuit board and a power source (not shown) disposed in the header plate 16. As shown in FIG. 4, energy chains 40 are employed to house the cabling connecting the signal lights 36 and selection lights 38 in the drawers, and move along horizontally along with the drawers 18 when the drawers are opened and closed.

Figure 2:
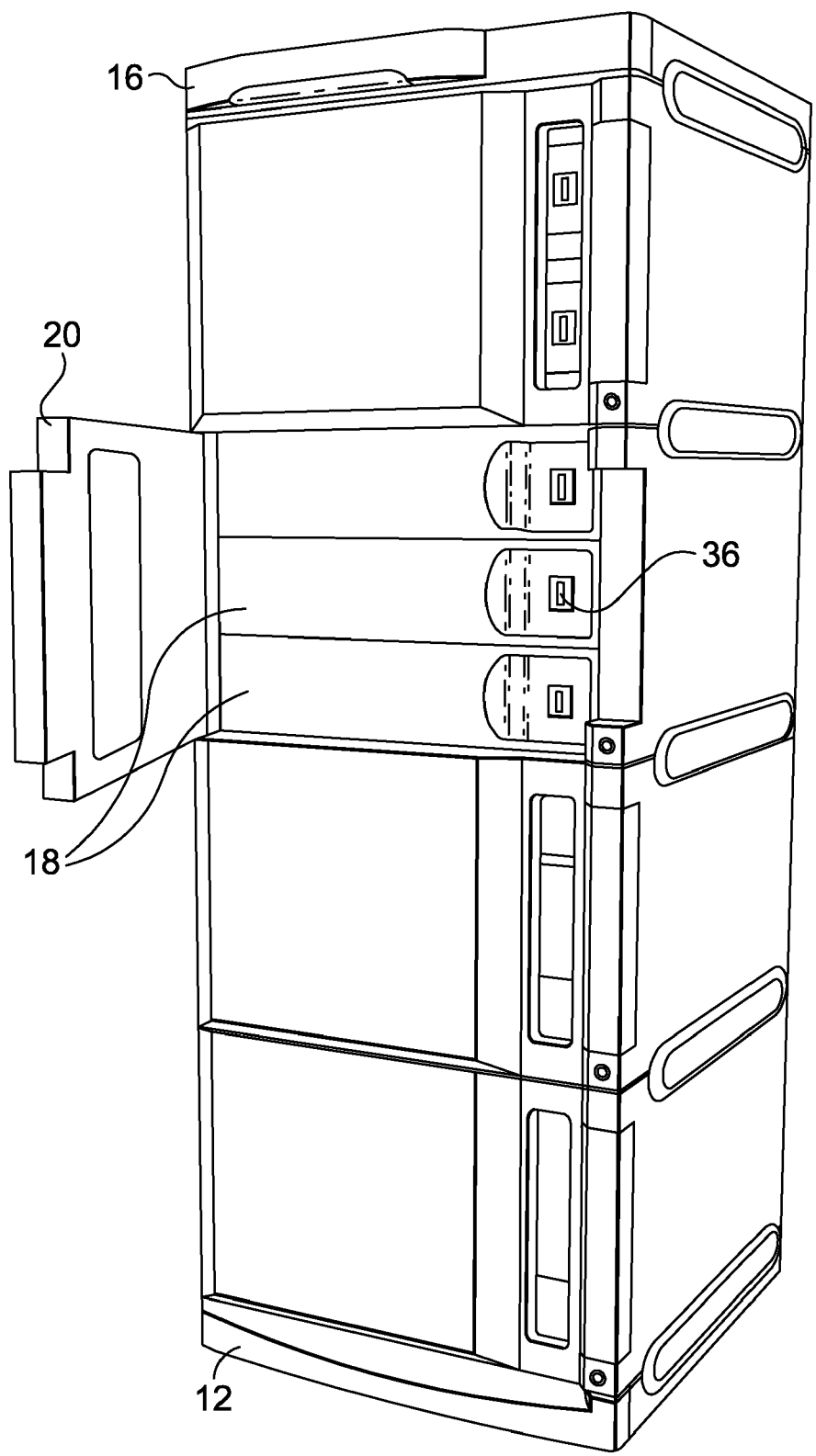
FIG. 2 is a front perspective view of a medication dispenser in accordance with an embodiment of the present invention having a front door opened to provide access to the drawers.

The modules 14 are configured to store multiple sized drawers 18 for medication storage and dispensing. For instance, referring to FIG. 1, a single large drawer may be associated with a module for storing particularly large items and equipment. Two drawers of equal or differing sizes may be associated with a particular module. Also, as illustrated in FIG. 2, three equally sized drawers may be housed within a module. It should be noted that drawer configurations different than those shown in FIGS. 1-5 may be employed in various embodiments of the invention (e.g., different drawer sizes, different number of drawers, different compartment configurations, etc.).

Figure 5:
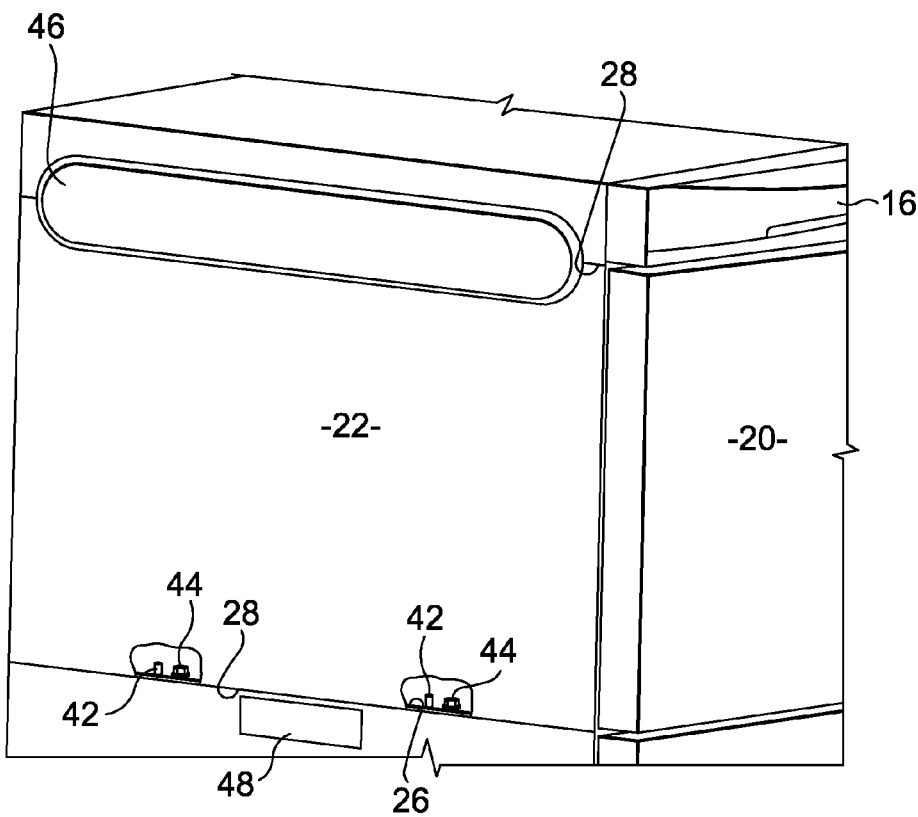
FIG. 5 is a side perspective view of a medication dispenser in accordance with an embodiment of the present invention with sections removed to demonstrate the assembly of the modules of the medication dispenser.

In an embodiment of the invention, as shown in FIG. 1, four modules 14 are stacked between the footer plate 12 and the header plate 16. With reference to FIG. 5, each module 14 includes a placement handle 48. The modules 14 are aligned to one another by a series of locating pins 42 extending from the top 26 of the lower module, and received within the bottom 28 of the upper module. Once located, a series of bolts 44 secure the modules one to another. The lowest module and the footer plate, and the uppermost module and the header plate, may be secured to one another in a similar manner. A series of cover strips 46 are secured on the exterior of the sidewalls 22 where each module is connected to another module, the header plate or the footer plate. In embodiments, the cover strips 46 are made of plastic, and overlay the seams to provide a unitary look to the device 10. Any number of modules 14 may be employed from a single module to a stack of four or more modules. The design allows a common construction for high volume areas of a hospital requiring a stack of multiple modules and lower volume areas of a health care provider in which a single module may effectively serve the population of recipients of care.

Referring again to FIG. 3, to stock the medication dispenser 10, medical items such as, for example, medications are initially placed into compartments 34. When medical items are placed into each compartment 34, the medical items and compartments 34 are identified to a computer system, which associates the medical items with their corresponding compartments 34. For instance, a compartment 34 may be identified to the computer system by reading a bar code located on, or associated with, the compartment 34 or by manually entering a compartment identifier. Similarly, in some embodiments, each medication or supply may be provided in a package having an identification marking, such as a bar code, an RFID tag, or some other identifier. A medical item may then be identified to the computer system by reading the bar code or RFID tag located on the medication package or by manually entering an identifier associated with the medical item.

After medications or supplies have been placed into compartments 34, the drawers 18 are slid into the closed position, and locked into place by locks (not shown) in electrical connection with the master circuit board and a power source (not shown) disposed in the header plate 16. The front doors 20 are also closed and locked.

Figure 3:
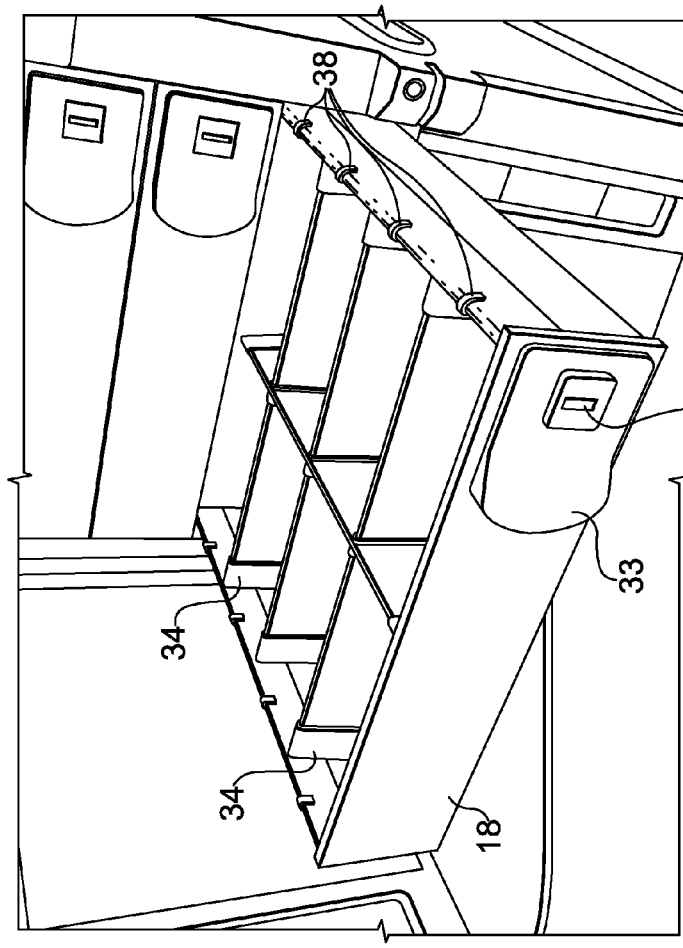
FIG. 3 is a front perspective view of a medication dispenser in accordance with an embodiment of the present invention having a front door opened and one drawer in an open position.

When a medication or supply is to be dispensed from the medication dispenser 10, a medication or supply is initially selected, for instance, by a clinician interacting with a computer system associated with the medication dispenser 20. The computer system accesses information associating medications or supplies with the location of the medication or supply. Specifically, the computer system determines the location of the module 14, drawer 18 and compartment 34 within which the relevant item is located. Next, the computer system communicates to the processor located in the header plate 16. The processor sends a signal to illuminate the signal light 26 of the appropriate drawer from which an item is to be retrieved. The user can visually identify the signal light 26 through the window 32. Also, in response to the signal, the front door 20 of the module within which the desired medication or supply is located is unlocked. The lock to the appropriate drawer 18 is unlocked, too, and drawer 18 with the illuminated signal light 26 is pulled open to the position as shown in FIG. 3. The processor also sends a signal to illuminate the appropriate selection light 38 to direct to the user to the appropriate compartment 34 in the appropriate drawer 18. In an embodiment, the process is repeated until each of the relevant medications and supplies are removed from the device 10. In some embodiments, multiple selection lights and signal lights may be illuminated simultaneously to allow the user to remove multiple items. In embodiments, the user may provide feedback to the computer system to verify that a specific medication or supply has been removed from the device.

As indicated previously, a computer system is provided for controlling the operation of the medication dispenser 10. In some embodiments, the computer system includes a computing device dedicated to the medication dispenser 10. The medication dispenser computing device may receive inputs, such as inputs associated with loading and medication-dispensing operations. Based on the inputs, the medication dispenser computing device controls the processor of device 10 and thus the locks, signal lights and selection lights of the present invention.

In some embodiments, the medication dispenser computing device may act as a stand-alone device such that the medication dispenser computing device maintains all data necessary for operating the medication dispensing operations of the medication dispenser 10. In other embodiments, however, the medication dispenser computing device operates within a distributed clinical computing environment. In particular, the medication dispenser computing device may be interfaced with or integrated into a medical information computer system. The medical information computing system may be a comprehensive computing system within a clinical environment such as the exemplary medical information computing system environment 200 shown in FIG. 20. It will be understood and appreciated by those of ordinary skill in the art that the illustrated medical information computing system environment 200 is merely an example of one suitable computing environment and is not intended to suggest any limitation as to the scope of use or functionality of the invention. Neither should the medical information computing system environment 202 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

Figure 6:
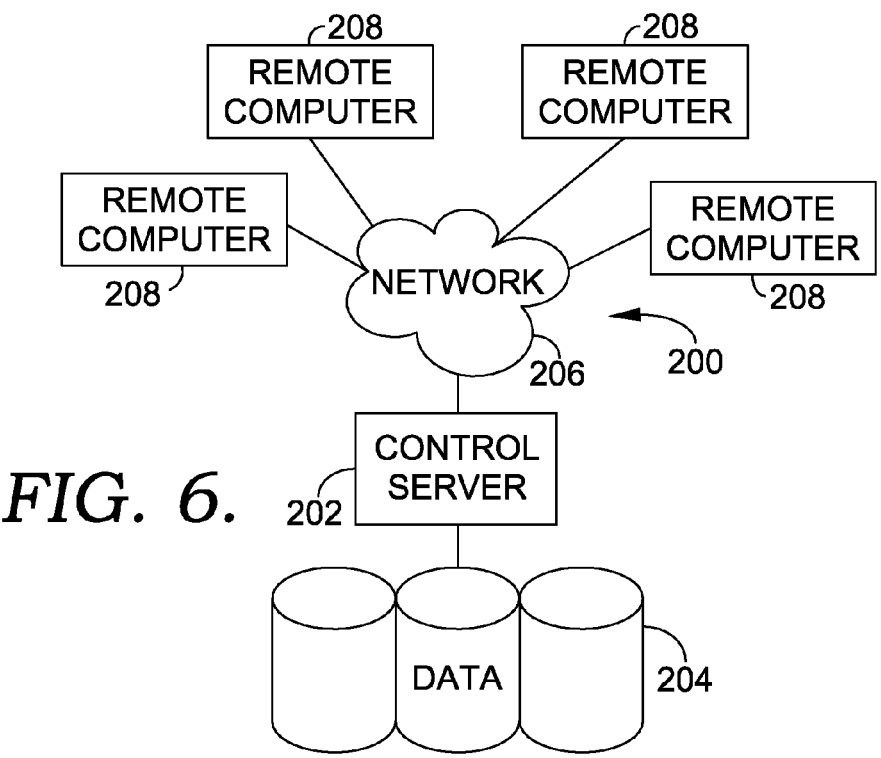
FIG. 6 is a block diagram of an exemplary medication information computing environment suitable for use in implementing the present invention.

With continued reference to FIG. 6, the exemplary medical information computing system environment 200 includes a general purpose computing device in the form of a server 202. Components of the server 202 may include, without limitation, a processing unit, internal system memory, and a suitable system bus for coupling various system components, including database cluster 204, with the server 202. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 202 typically includes, or has access to, a variety of computer readable media, for instance, database cluster 204. Computer readable media can be any available media that may be accessed by server 202, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 202. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 204, provide storage of computer readable instructions, data structures, program modules, and other data for the server 202.

The server 202 may operate in a computer network 206 using logical connections to one or more remote computers 208. Remote computers 208 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 208 may also be physically located in non-traditional medical care environments so that the entire health care community may be capable of integration on the network. The remote computers 208 may be personal computers, servers, routers, network PCs, peer devices, other common network nodes, or the like, and may include some or all of the components described above in relation to the server 202. The devices can be personal digital assistants or other like devices.

Exemplary computer networks 206 may include, without limitation, local area networks (LANs) and/or wide area networks (WANs). Such networking environments are commonplace in offices, enterprise-wide computer networks, intranets, and the Internet. When utilized in a WAN networking environment, the server 202 may include a modem or other means for establishing communications over the WAN, such as the Internet. In a networked environment, program modules or portions thereof may be stored in the server 202, in the database cluster 24, or on any of the remote computers 208. For example, and not by way of limitation, various application programs may reside on the memory associated with any one or more of the remote computers 208. It will be appreciated by those of ordinary skill in the art that the network connections shown are exemplary and other means of establishing a communications link between the computers (e.g., server 202 and remote computers 208) may be utilized.

In operation, a user may enter commands and information into the server 202 or convey the commands and information to the server 202 via one or more of the remote computers 208 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 202. In addition to a monitor, the server 202 and/or remote computers 208 may include other peripheral output devices, such as speakers and a printer.

Although many other internal components of the server 202 and the remote computers 208 are not shown, those of ordinary skill in the art will appreciate that such components and their interconnections are well known. Accordingly, additional details concerning the internal construction of the server 202 and the remote computers 208 are not further disclosed herein.

By interfacing and/or integrating a medication dispensing computing device with a comprehensive medical information computing system, such as the medical information computing system 200 of FIG. 6, a number of advantages may be realized. For example, the medication dispensing clinical device may be interfaced with or otherwise access computing devices and/or computing systems in a variety of different clinical domains within a healthcare environment. By way of example only and not limitation, the medical information computing system 200 may include a clinical laboratory system, a pharmacy system, a radiology system, and a hospital administration system. Accordingly, the medical information computing system 200 provides a unified computing architecture that is able to access and aggregate clinical information from a variety of different clinical domains and make the clinical information available to the medication dispensing computing device. In an embodiment, the medical information computing system 200 may store clinical information from different clinical domains in a patient-centric electronic medical record (including an electronic medication administration record) accessible to multiple devices within the system 200, including the medication dispensing computing device. Accordingly, medication dispensing may be automated and clinician workflow may be supported from medication prescribing through medication dispensing and administration. As such, a closed process may be provided that delivers increased patient safety throughout the medication process, greater speed in the medication dispensing process, and improved efficiency for clinicians.

The present invention has been described in relation to particular embodiments, which are intended in all respects to be illustrative rather than restrictive. Alternative embodiments will become apparent to those of ordinary skill in the art to which the present invention pertains without departing from its scope. Substitutions may be made and equivalents employed herein without departing from the scope of the invention as recited in the claims. It will be understood that certain features and subcombinations are of utility and may be employed without reference to other features and subcombinations. This is contemplated and within the scope of the claims.

What is claimed is:

1. A method for dispensing medical items, wherein medical items comprise medications and supplies, the method comprising:

providing a dispensing unit that includes a plurality of stackable modules arranged in a vertical stack, each of the plurality of stackable modules having a top, a bottom, a rear wall, side walls, and a lockable door with a transparent window disposed therein, wherein a first one of the plurality of stackable modules is aligned to a second one of the plurality of stackable modules by a series of locating pins extending from the top of the first module and being received within the bottom of the second module, and wherein each of the plurality of stackable modules comprises an environment in which medical items can be stored; and further wherein each of the plurality of stackable modules comprises at least one drawer having a signal light attached to a front side of the drawer so that the signal light is visible through the transparent window when the door is in a closed position, and at least one compartment defined within each drawer;

receiving a user selection of a medical item, the user selection comprising an item identifier corresponding to the selected medical item;

determining a location identifier associated with the item identifier, wherein the location identifier corresponds to a compartment in which the selected medical item is located;

illuminating the signal light associated with the drawer containing the compartment in which the selected medical item is located; and providing access to the compartment in which the selected medical item is located, wherein providing access comprises unlocking the module door.

2. The method of claim 1, wherein the plurality of modules comprises a vertical stack of two or more modules.

3. The method of claim 1, further comprising illuminating a selection light associated with the compartment in which the selected medical item is located.

4. The method of claim 1, further comprising providing a computer system that controls access to the compartment in which the selected medical item is located.

5. The method of claim 4, wherein the computer system comprises a dispenser computing device that maintains data necessary for providing access to medical items.

6. The method of claim 5, wherein the dispenser computing device operates within a distributed clinical computing environment.

7. The method of claim 1, wherein providing access to the compartment in which the selected medical item is located further comprises unlocking the drawer containing the compartment in which the selected medical item is located.

8. A method for dispensing medical items, wherein medical items comprise medications and supplies, the method comprising:

providing a dispensing unit comprising a plurality of stackable modules arranged in a vertical stack and a computing device, each of the plurality of stackable modules having a top, a bottom, a rear wall, side walls, and a lockable door with a transparent window disposed therein, wherein a first one of the plurality of stackable modules is aligned to a second one of the plurality of stackable modules by a series of locating pins extending from the top of the first module and being received within the bottom of the second module, and wherein each of the plurality of stackable modules comprises an environment in which medical items can be stored; and further wherein each of the plurality of stackable modules comprises at least one drawer having a signal light attached to a front side of the drawer so that the signal light is visible through the transparent window when the door is in a closed position, and at least one compartment defined within each drawer;

receiving a user selection of a medical item, the user selection comprising an item identifier corresponding to the selected medical item, wherein the user selection is received from a server that is communicatively coupled to the computing device, and further wherein the user selection is entered into the server via a remote computer;

determining a location identifier associated with the item identifier, wherein the location identifier corresponds to a compartment in which the selected medical item is located;

illuminating the signal light associated with the drawer containing the compartment in which the selected medical item is located; and providing access to the compartment in which the selected medical item is located, wherein providing access comprises unlocking the module door.

9. The method of claim 8, further comprising illuminating a selection light associated with the compartment in which the selected medical item is located.

10. The method of claim 8, wherein the computing device controls access to the compartment in which the selected medical item is located, wherein a first bar code is associated with the compartment.

11. The method of claim 10, wherein the medical item includes a package having a second bar code.

12. The method of claim 11, further comprising placing the medical item in the compartment.

13. The method of claim 12, further comprising:
reading the second bar code to identify the medical item to the computing device; and
reading the first bar code to identify the compartment to the computing device, wherein the computing device associates the compartment with the medical item.

14. A method for dispensing medical items, wherein medical items comprise medications and supplies, the method comprising:
providing a dispensing unit comprising a plurality of stackable modules arranged in a vertical stack and a computing device, each of the plurality of stackable modules having a top, a bottom, a rear wall, side walls, and a lockable door with a transparent window disposed therein, wherein a first one of the plurality of stackable modules is aligned to a second one of the plurality of stackable modules by a series of locating pins extending from the top of the first module and being received within the bottom of the second module, and wherein each of the plurality of stackable modules comprises an environment in which medical items can be stored; and further wherein each of the plurality of stackable modules comprises at least one drawer having a signal light attached to a front side of the drawer so that the signal light is visible through the transparent window when the door is in a closed position, and a compartment defined within each drawer, wherein a first bar code is associated with the compartment;
placing a medical item in the compartment, wherein the medical item includes a package having a second bar code;
reading the second bar code to identify the medical item to the computing device;
reading the first bar code to identify the compartment to the computing device, wherein the computing device associates the compartment with the medical item;
receiving a user selection of the medical item, the user selection comprising an item identifier corresponding to the selected medical item;
determining a location identifier associated with the item identifier, wherein the location identifier corresponds to the compartment in which the selected medical item is located;
illuminating the signal light associated with the drawer containing the compartment in which the selected medical item is located; and
providing access to the compartment in which the selected medical item is located, wherein providing access comprises unlocking the module door.

15. The method of claim 14, wherein the user selection is received from a server that is communicatively coupled to the computing device.

16. The method of claim 15, wherein the user selection is entered into the server via a remote computer.

17. The method of claim 16, wherein the computing device maintains data necessary for providing access to medical items.

18. The method of claim 17, wherein the computing device operates within a distributed clinical computing environment over a wide-area-network (WAN).

* * * * *